US012758789B2

(12) United States Patent
Moreau-Gobard et al.

(10) Patent No.: US 12,758,789 B2
(45) Date of Patent: Oct. 13, 2026

(54) SYSTEMS AND METHODS FOR DETERMINING THERAPEUTIC NEUROSTIMULATION THRESHOLDS

(71) Applicant: Magnus Medical, Inc., Burlingame, CA (US)

(72) Inventors: Romain Moreau-Gobard, Austin, TX (US); Armani Porter, Pikesville, MD (US); Brandon S. Bentzley, Half Moon Bay, CA (US); Thibaut Loysel, Nantes (FR); Yann Picard, San Francisco, CA (US)

(73) Assignee: Magnus Medical, Inc., Burlingame, CA (US)

( * ) Notice: Subject to any disclaimer, the term of this patent is extended or adjusted under 35 U.S.C. 154(b) by 482 days.

(21) Appl. No.: 18/523,638

(22) Filed: Nov. 29, 2023

(65) Prior Publication Data

US 2024/0207633 A1 Jun. 27, 2024

Related U.S. Application Data

(60) Provisional application No. 63/450,338, filed on Mar. 6, 2023, provisional application No. 63/385,367, filed on Nov. 29, 2022.

(51) Int. Cl.

| | |
|---|---|
| ***A61N 2/02*** | (2006.01) |
| ***A61N 2/00*** | (2006.01) |
| ***G16H 20/40*** | (2018.01) |

(52) U.S. Cl.

CPC .............. *A61N 2/02* (2013.01); *A61N 2/006* (2013.01); *A61N 2/008* (2013.01); *G16H 20/40* (2018.01)

(58) Field of Classification Search

CPC .......... A61N 2/02; A61N 2/006; A61N 2/008; G16H 20/40; G16H 30/40

See application file for complete search history.

(56) References Cited

U.S. PATENT DOCUMENTS

| | | | |
|---|---|---|---|
| 2014/0172041 | A1 | 6/2014 | Draghici et al. |
| 2019/0201707 | A1 | 7/2019 | Stubbeman |
| 2020/0206503 | A1 | 7/2020 | Ganzer et al. |

FOREIGN PATENT DOCUMENTS

| | | |
|---|---|---|
| WO | 2024118820 A1 | 6/2024 |

OTHER PUBLICATIONS

Cole et al. (Stanford Neuromodulation Therapy (SNT): A Double-Blind Randomized Controlled Trial. Am J Psychiatry; 179:2, 132-141) (Year: 2022).*

International Search Report and Written Opinion for International Application No. PCT/US2023/081659, Search completed Mar. 18, 2024, Mailed Apr. 18, 2024, 11 Pgs.

International Preliminary Report on Patentability for International Application PCT/US2023/081659, Report issued May 27, 2025, Mailed Jun. 12, 2025, 10 Pgs.

* cited by examiner

*Primary Examiner* — Kaylee R Wilson

(74) *Attorney, Agent, or Firm* — KPPB LLP

(57) ABSTRACT

Described herein are methods and systems to facilitate treatment of neurological and psychiatric disorders using transcranial magnetic stimulation. The methods and systems may provide for the decrease in the time needed to determine the motor threshold. The methods and systems generally reduce the complexity of obtaining a motor threshold while providing a more reliable and less intensive motor threshold determination process.

17 Claims, 10 Drawing Sheets

FIG. 8
magnusmedical
Fernando Alongname...
PATIENT ID
BIRTH DATE
REFERRING PHYS
CLINICAL SITE
COIL PLACEMENT
MOTOR THRESHOLD LOCATION
MOTOR THRESHOLD LEVEL
COIL ORIENTATION
MOTOR THRESHOLD LEVEL 34%
REDO
NO TWITCH
TWITCH OBSERVED

FIG. 9
magnus medical
Tammy Morton 1
TREATMENT SESSIONS
DAY 1
0 seconds Left in Current Session
10% of Todays Sessions Completed
READY TO PROCEED

SYSTEMS AND METHODS FOR DETERMINING THERAPEUTIC NEUROSTIMULATION THRESHOLDS

CROSS-REFERENCE TO RELATED APPLICATIONS

This application claims priority to U.S. Provisional Application No. 63/450,338, filed on Mar. 6, 2023, and U.S. Provisional Application No. 63/385,367, filed on Nov. 29, 2022, each of which are hereby incorporated by reference in its entirety.

TECHNICAL FIELD

This application generally relates to systems and methods for determining a stimulation threshold when delivering neurostimulation therapy for treating a neurological or a psychiatric disorder.

BACKGROUND

Transcranial Magnetic Stimulation (TMS) is a non-invasive medical procedure where strong magnetic fields are utilized to stimulate specific areas of an individual's brain to treat neurological or psychiatric disorders. To improve the accuracy, reliability, and repeatability of TMS treatments, neuronavigation systems have been developed. For example, optically or magnetically tracked neuronavigation systems have been developed that allow a user to position a TMS coil over a specified stimulation target location based on the brain image (e.g., an MRI image) of a patient. Neuronavigation requires an accurate measurement of the positions and orientations of the head of an individual and the equipment used for treatment. To determine the physical position of the stimulation target on the working space, the transform of the patient's MRI data usually needs to be estimated so that it is accurately aligned with the patient's head (registration). Regardless of the exact physical position of the target or application, one of the most influential parameters in all TMS applications is the intensity at which the stimulation is applied. For example, stimulation intensity that is too low may not activate the target area. In contrast, stimulation intensity that is too high may activate the target area and the neighboring regions, resulting in a loss of the targeted outcome (e.g., an undesired brain state).

TMS of the motor cortex has a well-established role in clinical neurophysiology and is generally used to assess the conduction of the descending cortico-nuclear and cortico-spinal connection. The motor cortex, and specifically the hand knob area of the premotor cortex, comprised of the premotor cortex hand area and the adjacent dorsal premotor cortex, is often a target area for neurostimulation as changes in motor activation and excitability can be readily assessed by recording motor evoked potentials. In clinical practice, the intensity of TMS may be individually adjusted to the cortical motor threshold (MT), which may be considered as the minimal intensity of motor cortex stimulation required to elicit a reliable motor evoked potential of minimal amplitude in the target muscle, or a visible twitch. It has been reported that the MT determination based on visual observation is associated with high intra- and inter-rater variability (Rossini, PM, Bruke, D, Chen, R, et.al. *Clin Neurophysiol*, 2015, 126: 1071-1107). However, use of the MT has become the standard for determining TMS dose due to its relationship with safety in regard to the possibility of inadvertent seizure, and to its efficacy and reproducibility in stimulating the motor cortex.

Traditional methods of determining a resting MT involve finding a threshold of either visible movement or electromyogram (EMG) motor evoked potentials. Traditional methods for measurement of MTs are generally time intensive, cumbersome, and require determining MTs using multiple stimuli approached from supramaximal to subthreshold and averaging the two (Rossini, PM, Bruke, D, Chen, R, et.al. *Clin Neurophysiol*, 2015, 126:1071-1107). For example, in the traditional method, pulses may be delivered beginning with an intensity of 50% TMS machine output. The resting MT (rMT) is defined as the average of two values referred to as the lower and upper rMT (LT and UT, respectively). The LT is the first value identified and is defined as the intensity at which less than three of the six trials resulted in a response. Intensity is decreased in 2% decrements of maximum TMS machine output until the LT is found. Once the LT is obtained, the TMS intensity is reduced 4% of maximum machine output below the LT value and then increased in 2% increments until the first value associated with a successful response for three of six trials is identified. This is defined as the UT. The MT is estimated as the mean of the lower (LT=largest stimulus strength with no success within less than 3 of 6 trials) and the upper threshold (UT=smallest stimulus strength with at least 3 successes within 6 trials) (Mishory A, Molnar (, Koola J, et.al., *J ECT*, 2004, 20:160-165).

To reduce the time and the number of stimuli needed to determine the MT, a maximum-likelihood strategy has been developed using a mathematical algorithm called parameter estimation by sequential testing (PEST). The ML-PEST method surrounds the threshold depending on the single response from each intensity setting. The ML-PEST method may yield EMG-based MT results comparable to traditional methods in terms of accuracy and in less time (Awiszus F. *Suppl. EEG Clin Neurophysiol*, 2003, 56:13-23). In an extension of the ML-PEST study conducted by Awiszus, visual determination of the MT was used, and the ML-PEST algorithm was incorporated into the computer system controlling the neurostimulation generator to fully automate the ML-PEST technique. The ML-PEST approach was found to be significantly faster and used fewer pulses to estimate the MT (Mishory A, Molnar C, Koola J, et.al., *J ECT*, 2004, 20:160-165).

To further reduce the time and the number of stimuli needed to determine the MT, it may be useful to incorporate a mathematical model into the computer system controlling the neurostimulation generator. This model may be trained on data from prior MT sessions that includes information related to the geographic location of an individual's hand knob and MT data from prior MT sessions (e.g., ML-PEST data). This may be important as the computer system controlling the neurostimulation generator can only estimate the location and position of the hand knob of a patient based on MRI data. However, factors such as dehydration may cause the location and/or position of a patient's hand knob to move to a location that is different than anticipated. Alternatively, brain abnormalities due to genetics or a prior injury may cause the location and/or position of a patient's hand knob to be misidentified.

Thus, it would be useful to have new systems and methods that provide a simple and less time consuming MT determination for TMS. It would also be beneficial to simplify navigation of the TMS coil to the motor cortex target location.

SUMMARY

Described herein are systems and methods for neuronavigation useful for determining a stimulation threshold, e.g., a motor stimulation threshold, when delivering neurostimulation therapy for treating a neurological or a psychiatric disorder. Neuronavigation for TMS generally requires an accurate measurement of the positions and/or orientations of the patient's head and the equipment used for treatment. However, regardless of the exact physical position of the target or application, one of the most useful parameters in all TMS applications is the intensity at which the stimulation is applied.

As previously mentioned, to reduce the time and the number of stimuli needed to determine a cortical motor threshold (MT), it may be useful to incorporate a mathematical model into the computer system controlling the neurostimulation generator. This model may be trained on data from prior MT sessions that includes information related to the geographic location of a patient's hand knob and MT data from prior MT sessions (e.g., ML-PEST data), and used to estimate the location and position of a patient's hand knob based on MRI data. However, factors such as dehydration and abnormalities due to genetics or injury may cause the location and position of an individual's hand knob to move to a location different from that anticipated, as previously stated. Given this, the systems and methods described herein may utilize a model that analyzes hand knob and MT data from prior MT sessions, biosignals, genetics, and clinical data so that the system may more efficiently estimate the location of the hand knob during successive MT sessions.

To even further reduce the time and the number of stimuli needed to determine the MT, the model that may be incorporated into the computer system controlling the neurostimulation generator may give preference to regions of high elevation in the brain (e.g., gyruses). For example, during MT determination, the clinician may be guided to administer stimulations to regions of the hand knob that are closest to the coil as such regions would be most likely to elicit a hand twitch (including a finger twitch) due to charge roll-off.

In one variation, an interactive coil positioning procedure is implemented to determine a motor hand knob location and/or a MT. A coil positioning screen may first be provided on a display. The interactive coil positioning may help the user to position the coil close to the motor hand knob location. The computer screen may then display a model of the patient's head, which may aid in visually guiding placement of the coil for determination of a MT.

In another variation, determination of the location of the motor hand knob may be visualized by mapping the location of the coil position on a two dimensional (2D) map. The motor threshold location screen may first be displayed. A 2D surface centered on the motor hand knob location may then be displayed on the screen. The 2D location of the coil may be represented by a "+" mark on the map. The user may initiate stimulation pulses delivered through the TMS coil. If the user moves the coil outside of the 2D surface, the user may be returned to the coil positioning screen. If a twitch is detected as a result of the stimulation pulse, a pulse marker may be placed on the 2D map. Once the motor hand knob location has been confirmed, the process for obtaining the MT may be initiated by the user.

Although the motor hand knob may be recognized on brain imaging data, such as MRI, it may be the case that a) the estimated position of the hand knob is in a different location or b) the estimated shape of the motor hand knob is different, therefore the position of the motor hand knob is in a different location than anticipated. To account for this, the clinician may be guided on the 2D map to administer pulses along a path that may be articulated in various shapes, such as the shape of a spiral. In this example, the origin of the spiral may be placed at the estimated center of the motor hand knob to minimize the amount of time that it takes to accurately determine the MT by maximizing the likelihood of receiving a hand or finger twitch. Instructions for the movement of the TMS coil to the desired target position may then be displayed on the screen so that the clinician may direct the coil to the initial target position (e.g., center of the spiral). Once the coil has reached the landmark, the clinician may be guided to search for the hand knob along the path (e.g., the spiral) that is superimposed onto the 2D map of the brain.

In some variations, preference may be given to sections of the path (e.g., spiral) that correspond to regions of high elevation in the brain (e.g., gyruses). In some cases, it may be possible that a clinician directed a pulse towards the motor hand knob without eliciting a hand or finger twitch. When this occurs, the pulse may have been directed towards a valley in the brain (e.g., sulcus), thus decreasing the likelihood of eliciting a hand or finger twitch due to charge roll-off. To overcome this problem, sections of preference on the aforementioned spiral may be identified by colors or shapes that signify regions of high elevation. Accordingly, clinicians may administer pulses at or near these regions in order to decrease the time necessary to determine a MT.

In other variations, the maximum likelihood parameter estimation by sequential testing (ML-PEST) may be implemented to reduce the time and number of stimuli to find the MT. The ML-PEST algorithm may automatically modify pulse intensity (e.g., increase or decrease pulse intensity) based on visual confirmation of a hand or finger twitch. For example, following each pulse, the user may press a button indicating whether a twitch was observed or not. The results may then be mapped on a chart displayed on the screen. In some instances, a depth correction computation may also be performed when determining the treatment intensity.

In further variations, the systems and methods described herein may employ a mathematical model that is trained to identify the location at which the hand knob resides based on the location and the level of intensity of the stimulations that elicited a hand or finger twitch during prior MT sessions. This may be done so that subsequent MTs may be obtained more accurately, efficiently, and with greater consistency. These variations may also overcome those difficulties that arise when an individual's hand knob is in a location that differs from the conventionally recognized landmark in the precentral gyrus or has moved to a location that is different from that which was estimated based on brain imaging data.

In some variations, the method of delivering neurostimulation may include obtaining one or more MRI images of a head of a patient and interactively positioning a neurostimulation device at a target location on the head of the patient. The step of interactively positioning may include determining a location of a hand knob area of a motor cortex of the patient on the one or more MRI images using a machine learning algorithm; reviewing, by a user (e.g., a clinician), the location of the hand knob area determined by the machine learning algorithm; and optionally correcting, by the user (e.g., a clinician), the location of the hand knob area determined by the machine learning algorithm to a corrected hand knob area. Neurostimulation may then be delivered from the neurostimulation device at the target location to the hand knob area or the corrected hand knob area. Interactively positioning may further comprise viewing the head of the patient and a ghost image of a neurostimulation device on a screen of a neurostimulation system display, and while viewing the neurostimulation system display, guiding the neurostimulation device to the target location.

In other variations, the method for delivering neurostimulation may further comprise determining a motor threshold (MT) for the patient comprising creating a two dimensional (2D) map of an unfolded skull of the patient. The 2D map may comprise a spiral shape. Determining the MT may also include adjusting an intensity of the delivered neurostimulation, and/or observing whether the delivered neurostimulation results in a hand twitch.

The neurostimulation device may comprise any type of device suitable for delivering neurostimulation. In one variation, the neurostimulation device comprises a transcranial magnetic stimulation (TMS) coil. The neurostimulation delivered may be accelerated Theta-Burst Stimulation (aTBS), for example, accelerated intermittent Theta-Burst Stimulation (aiTBS) or accelerated continuous Theta-Burst Stimulation (acTBS).

The neurostimulation that is delivered may be used to decrease the time needed to determine the MT when treating a neurological disorder or a psychiatric. In other words, it may be used as part of the treatment for a neurological or a psychiatric disorder. Exemplary neurological disorders may include without limitation, Parkinson's disease, essential tremor, stroke, epilepsy, traumatic brain injury, migraine headache, cluster headache, chronic pain, or consequences of stroke. Exemplary psychiatric disorders may include without limitation, a depressive disorder, an anxiety disorder, post-traumatic stress disorder (PTSD), obsessive-compulsive disorder (OCD), an addiction, a substance use disorder, bipolar disorder, or schizophrenia. The anxiety disorder may be a generalized anxiety disorder, panic disorder, or a phobia. The phobia may be a social phobia or agoraphobia.

Neuronavigation systems for delivering neurostimulation to a patient are also described herein. The systems may generally be configured to deliver neurostimulation according to the methods described herein, and comprise a display; a neurostimulation device; and one or more processors configured to apply a machine learning algorithm to determine a location of the hand knob area of the patient. As previously stated, the neurostimulation device may comprise a transcranial magnetic stimulation (TMS) coil. The one or more processors may be configured to control one or more neurostimulation parameters. For example, the one or more neurostimulation parameters may include stimulation intensity. In some variations, the display of the system may include instructions for movement of the neurostimulation device to the target location.

DETAILED DESCRIPTION

Figure 1:
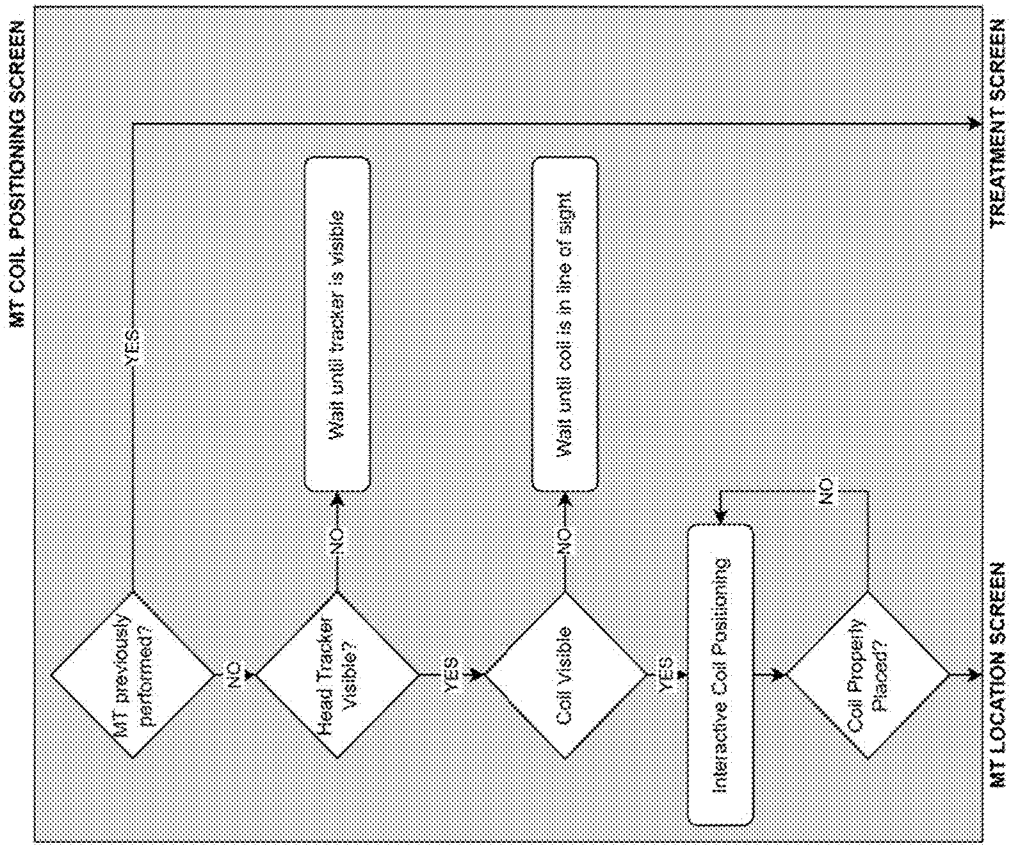
FIG. 1 is a flow chart depicting an exemplary method for positioning a transcranial magnetic stimulation coil on the head of a patient.

Described herein are systems and methods for neuronavigation that include one or more of neurostimulation device positioning and determining a stimulation threshold, e.g., a motor stimulation threshold when delivering neurostimulation therapy for treating a neurological or a psychiatric disorder. The neurostimulation device may be a coil configured to deliver transcranial magnetic stimulation (TMS). The systems may be configured to deliver neurostimulation therapy in various ways. For example, the neurostimulation may include accelerated intermittent Theta-Burst Stimulation (aiTBS) delivered in a plurality of sessions, as further described herein. Positioning of the neurostimulation device, delivery of neurostimulation, and determination of a motor stimulation threshold may be at least partially automated and may be based on the output of one or more machine learning algorithms.

In some variations, the methods for delivering neurostimulation may include obtaining one or more MRI images of a head of a patient and interactively positioning a neurostimulation device at a target location on the head of the patient. The methods may further comprise sending the one or more MRI images of the head of the patient to a cloud server. The step of interactively positioning may include determining a location of a hand knob area of the patient on the one or more MRI images using a machine learning algorithm, and reviewing, by a user of the neurostimulation device, the location of the hand knob area determined by the machine learning algorithm. Optionally, if the user considers the location of the hand knob area determined by the machine learning algorithm to be incorrect, the user may correct the location to a corrected hand knob area. Thereafter, neurostimulation may be delivered from the neurostimulation device at the target location to the hand knob area or the corrected hand knob area. The neurostimulation device may be a TMS coil.

In other variations, interactively positioning the neurostimulation device may further include viewing the head of the patient and a ghost image of the neurostimulation device on a display of a monitor of a neurostimulation system, where the ghost image overlaps the target location. While viewing the display, the neurostimulation device may be guided to the target location manually (e.g., by the user) or automatically, in a manner that is at least partially manual or automated, or may transition from manual to automated (or from automated to manual).

In further variations, e.g., when a TMS coil is used, the methods for interactive alignment of the TMS coil to a target location on the head of a patient for determination of the motor threshold may include: acquiring MRI image(s) of the head of a patient; sending the MRI image(s) of the head of a patient to a cloud server; detecting the anatomical location of the segment of the precentral gyrus known as the motor hand knob by analyzing the MRI of the head of a patient using a machine learning algorithm; reviewing by a human user the anatomical location detected by the machine learning algorithm and optionally correcting the location; and once the anatomic location of the motor hand knob is determined, projecting a point onto the surface of the skull identified on the MRI of the head of a patient. The skull may be segmented using the MRI anatomic data and the surface of the skin identified. Visibility of the head tracker placed on the head of a patient may then be confirmed, and if the tracker is not visible, the user may wait until the tracker is visible. Next, visibility of the coil may be confirmed, and if the coil is not visible the user may wait until the coil is visible. A projection technique using the normal to the skin may then be utilized such that the coil image is tangential to the patient's skull, and once both projected points are obtained, a search grid may be displayed on a 3D rendering of the patient's head having skin on the surface. A 'ghost' image of the coil may next be displayed on a TMS system screen to aid in guiding the coil to the target area.

In addition to positioning the neurostimulation device, the methods may also include determining a motor threshold (MT) for the patient. The methods may generally first comprise creating a two dimensional (2D) map of an unfolded skull of the patient in order to identify a hand knob area of the patient. The 2D map may comprise a spiral shape. In some instances, generating the 2D map may include identifying a skin surface on the one or more MRI images of the head of the patient, determining a line normal to the skin surface, and projecting a first point that may represent the hand knob area to a second point on the normal line. The second point may represent a center of the 2D map, e.g., the center of the spiral. A neurostimulation device may then be positioned over the second point and the hand knob area determined by moving the neurostimulation device along a path of the spiral starting from the center of the spiral.

Additionally or alternatively, the methods may include determining a motor threshold (MT) for the patient, where the MT may include adjusting an intensity of the delivered neurostimulation. In some variations, determining a MT may include observing whether the delivered neurostimulation results in a hand twitch. The neurostimulation that is delivered may be accelerated Theta-Burst Stimulation (aTBS), e.g., accelerated intermittent Theta-Burst Stimulation (aiTBS) or accelerated continuous Theta-Burst Stimulation (acTBS). The delivered neurostimulation may be used for treating a neurological disorder. Exemplary neurological disorders may include, without limitation, Parkinson's disease, essential tremor, stroke, epilepsy, traumatic brain injury, migraine headache, cluster headache, chronic pain, or consequences of stroke. Psychiatric disorders may also be treated with the delivered neurostimulation. For example, psychiatric disorders including, but not limited to a depressive disorder, an anxiety disorder, post-traumatic stress disorder (PTSD), obsessive-compulsive disorder (OCD), an addiction, a substance use disorder, bipolar disorder, or schizophrenia may be treated. The anxiety disorder may be generalized anxiety disorder, panic disorder, or a phobia. The phobia may be a social phobia or agoraphobia.

Figure 2:
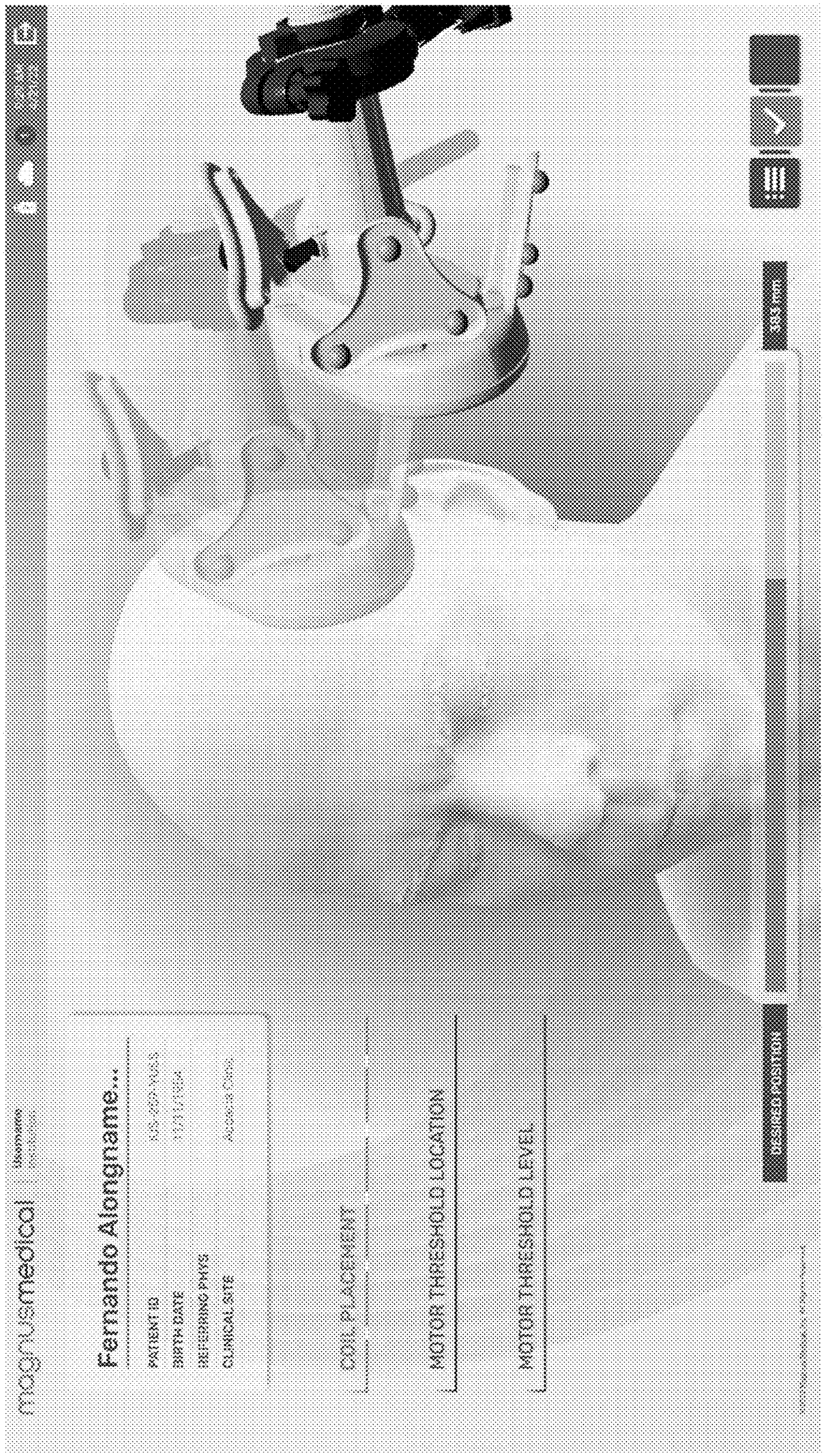
FIG. 2 depicts an exemplary display showing placement of a transcranial magnetic stimulation coil on a head of a patient.

Referring to FIG. 1, an exemplary method for facilitating transcranial magnetic stimulation (TMS) coil positioning with respect to a three dimensional (3D) rendering of a patient's head is illustrated. Prior to initiating TMS therapy of a patient, the clinician may view a motor threshold (MT) coil positioning screen of a display of a system monitor (e.g., a TMS system monitor). If the MT has been previously determined by a clinician, the clinician may skip the steps to position the coil and proceed to the treatment screen. If the MT was not previously determined, the clinician may confirm visibility of the TMS coil on the screen. Interactive coil positioning may then be performed and visualized on the screen. One or more computer processors may process data from one or more cameras positioned at a distance from a defined or predetermined neurostimulation target, one or more fiducial points affixed to the TMS coil, and one or more fiducial points on the head of a patient to compute the location of the TMS coil with respect to the head of the patient. The interactive coil positioning may be visualized on the coil positioning screen of the display, as shown in FIG. 2.

Interactive coil positioning may be accomplished using the following steps: a) an MRI of the patient to be treated may obtained; b) using the MRI, the anatomical location of the motor hand area may be determined (the segment of the precentral gyrus that most often contains the motor hand function appears as a knob-like structure that is shaped like an omega or epsilon in the axial plane, and like a hook in the sagittal plane); c) a machine learning algorithm may automatically find the most likely area for both the right and left motor hand area (or hand-knobs); d) a human user may review the machine learning algorithm result and optionally correct the location; e) once the location is determined, the point may be projected onto the surface of a 3D rendering of the skull of a patient, where the skull may first be segmented using the MRI anatomical data and the exact surface of the skin; f) a projection technique may use the normal to the skin so that the coil is tangential to the patient's skull; and g) once both projected points are obtained, a search grid may be displayed on the 3D rendering of the patient's skin where the display may be rendered as a "ghost" image of the coil, thus facilitating guiding the coil to that area.

In some variations, e.g., when functional connectivity is also to be assessed, fMRI (functional magnetic resonance imaging) may be used to obtain images of the brain of a patient. fMRI is an imaging modality that may be used to observe functional connectivity within the brain. However, this technology may be cumbersome to use due to its size, weight, and cost. Further, this instrument employs radiation to image the brain which may pose a safety risk for both patients and clinicians. Given this, it would be beneficial to have methods and systems for measuring functional connectivity that are safe, cost-effective, and easy to use. fNIRS (functional near-infrared spectroscopy) is an imaging modality that employs light to measure functional connectivity in the brain. This modality is cost-effective, light, and easy to use. Although fNIRS can capture these signals effectively, this imaging modality cannot measure depth. Without this capacity, a clinician is unable to administer treatment to a defined target. To circumvent this issue, ultrasound, as well as doppler variations, may be used in conjunction with fNIRS to assist a clinician in delivering treatment to the correct location. In another variation, doppler ultrasound may be used to measure functional connectivity. In some instances, this may be beneficial due to the superior temporal resolution of doppler ultrasound relative to other imaging modalities, such as fNIRS.

Referring back to FIG. 2, an example of a coil positioning screen is shown. The screen shows patient information and indicates the step in the motor thresholding process (e.g., green indicates "Coil Placement"). To facilitate TMS coil positioning for delivery of TMS at a defined target (e.g., the motor hand knob) to determine MT, a model of the patient's head may first shown with a ghost image of coil placement on the location of the skull. The progress toward reaching the desired coil position may be tracked at the bottom of the screen. Once the coil is properly aligned with respect to the desired coil position displayed on the model of the patient's head, the coil may change in color, e.g., the coil may turn green, red, yellow, blue, etc. In FIG. 2, the coil turns green in color when properly positioned.

The methods described herein may also include determining a motor threshold of a patient. In general, the methods may employ displaying a three-dimensional (3D) rendering of a head of the patient on a monitor of a neuronavigation system, generating a two-dimensional (2D) map of a brain of the patient from the 3D rendering, determining a hand knob area of the brain on the 2D map, aligning a neurostimulation device with the hand knob area, and delivering neurostimulation to the hand knob area. After delivering neurostimulation, a motor threshold of the patient may be determined based on whether a body part of the patient is affected by twitching.

In some variations, the 3D rendering may be an image obtained using magnetic resonance imaging and generating the 2D map may include creating a representation of an unfolded skull having a spiral superimposed thereon. Determining the hand knob area may then comprise moving the neurostimulation device along a path of the spiral starting from the center of the spiral. Movement or alignment of the neurostimulation device may be manually performed or automated. The neurostimulation device may comprise any device configured to deliver neurostimulation. In one variation, the neurostimulation device comprises a transcranial magnetic stimulation (TMS) coil.

The body part affected by twitching may include a portion of a face of the patient. For example, the portion of the face affected by twitching may comprise an eye, a cheek, a lip, a nose, or a combination thereof. In other instances, the body part affected by twitching may be an arm, a wrist, a hand, or a finger of the patient, or a combination thereof. In further instances, the body part affected by twitching may be a leg, an ankle, a foot, or a toe of the patient, or a combination thereof.

Additionally or alternatively, the methods described herein may include determining an intensity of the neurostimulation tolerable by the patient. A parameter estimation by sequential testing (PEST) process may be used in determining the intensity of neurostimulation.

Figure 3:
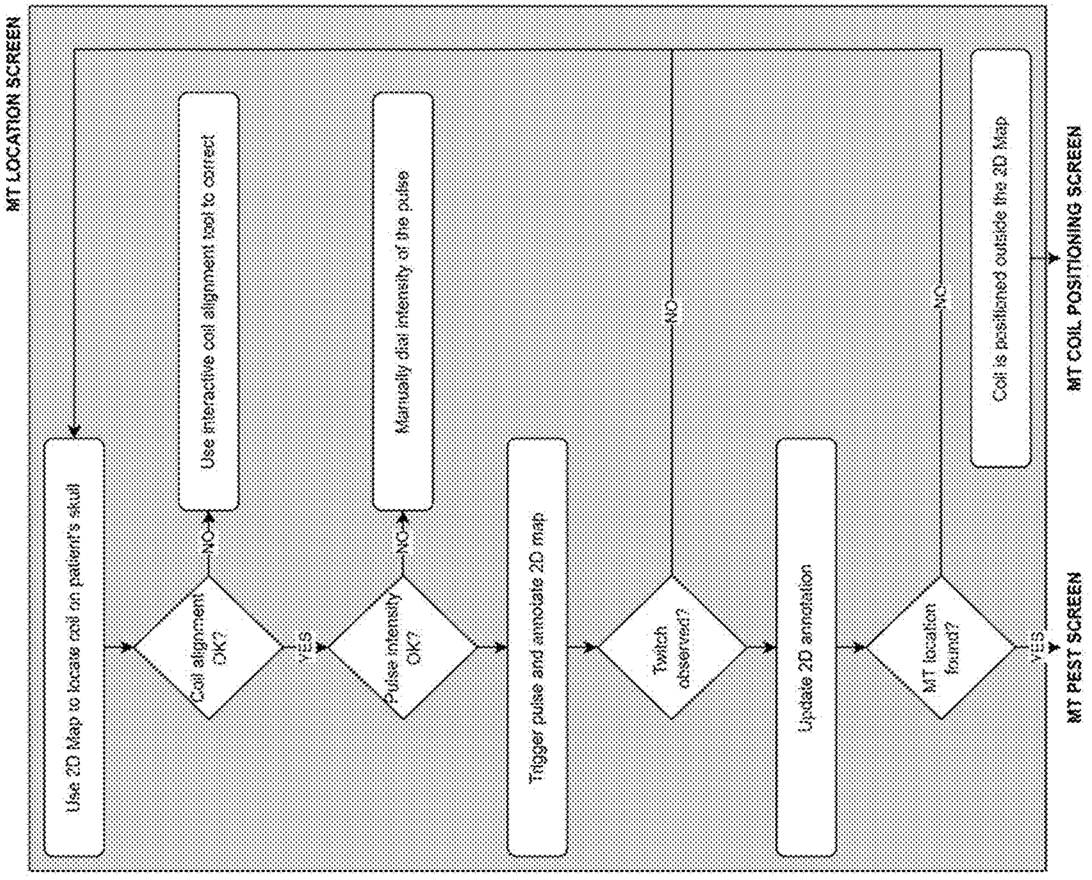
FIG. 3 is a flow chart depicting an exemplary method for determining the location of the motor cortex.
Figure 5:
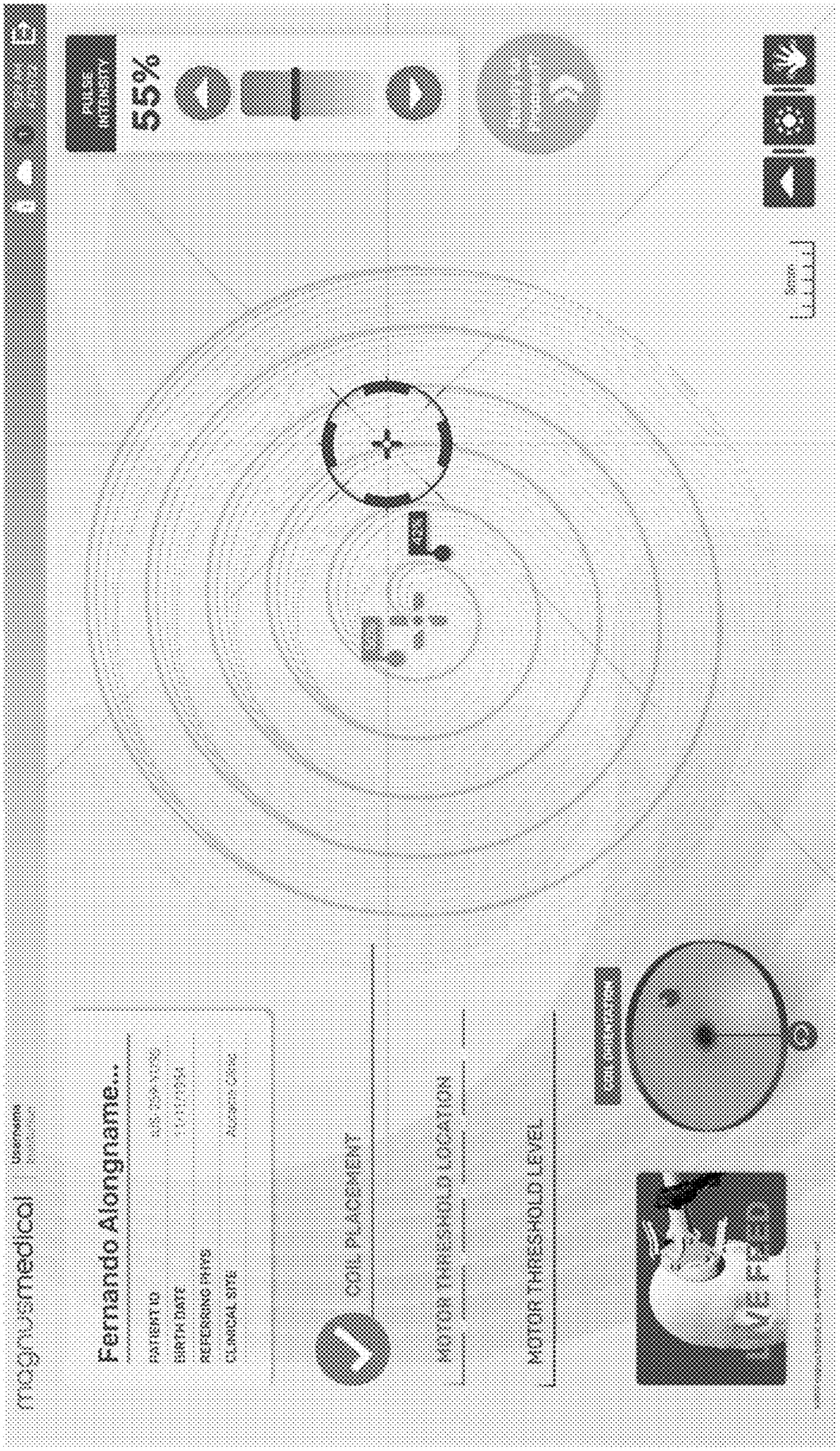
FIG. 5 depicts an exemplary display showing a 2D map of an unfolded patient skull for determining motor threshold location.

FIG. 3 depicts a flow chart to facilitate TMS coil positioning to deliver TMS at a defined target (motor hand knob) to determine the motor threshold. Prior to initiating TMS therapy, the clinician may view the MT Coil Positioning screen (FIG. 2) on the display to check whether the coil is aligned with the ghost coil on the display. Once coil alignment is determined, the clinician may navigate to the MT Location screen. The clinician confirms coil alignment and initiates the first stimulus to determine MT. If the coil was not aligned, the clinician may confirm alignment of the TMS coil on the display. Once the stimulus is delivered, the clinician may confirm with the patient that the intensity is acceptable. If a twitch is observed on the display, the clinician may indicate whether a hand twitch was observed due to stimulation of the motor hand knob. A button at the bottom of the MT Location screen (FIG. 5) may be pressed to indicate twitch or no twitch. The computer processor processes the twitch data entered and a mark may be annotated on the 2D map displayed on the screen (FIG. 5).

Figure 4:
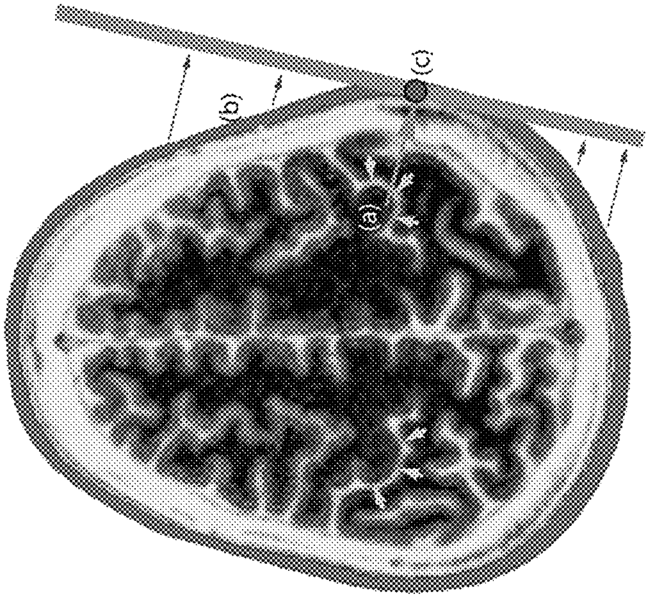
FIG. 4 illustrates an exemplary projection method used to create a two dimensional (2D) map of an unfolded patient skull.
Figure 6:
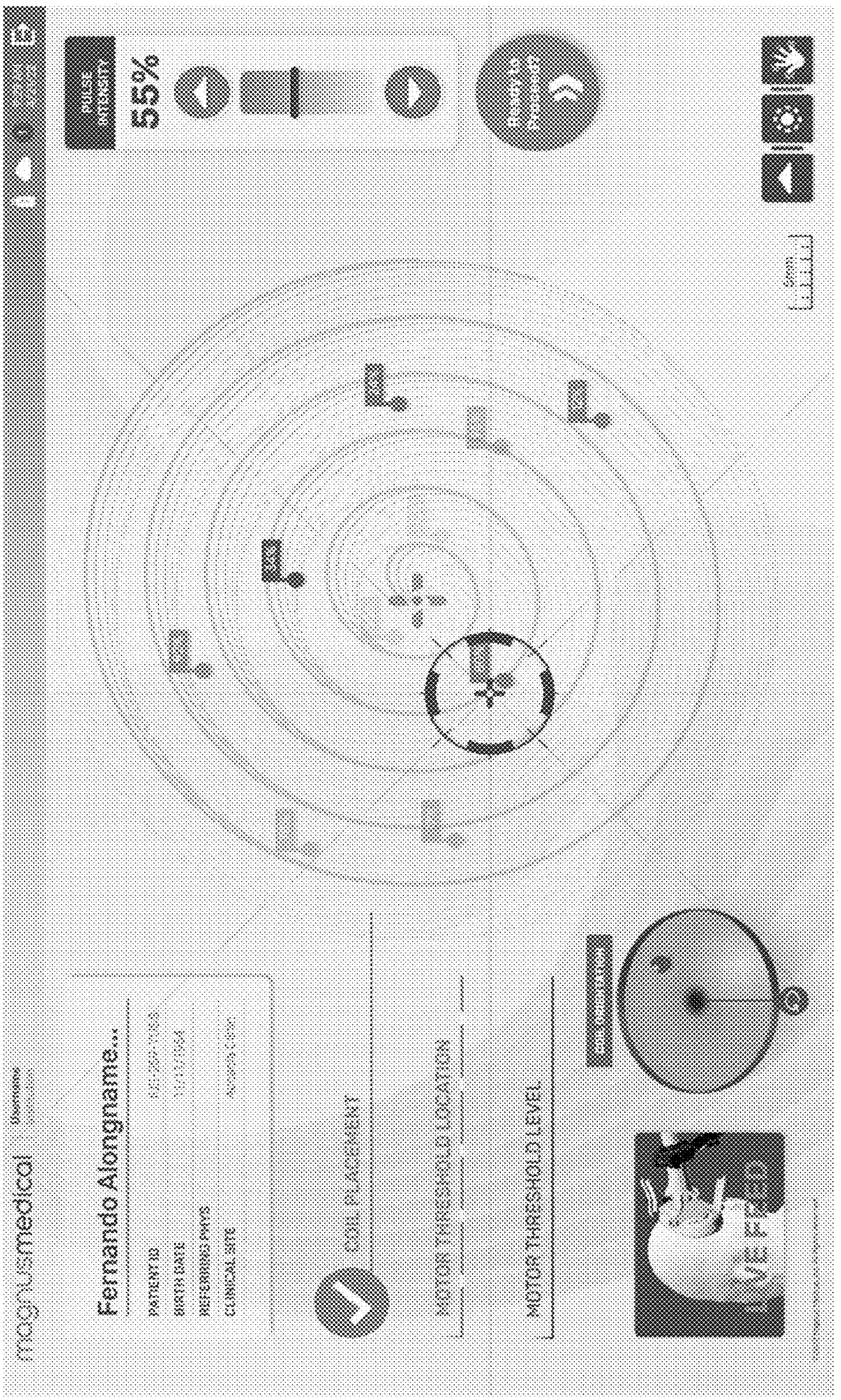
FIG. 6 depicts another exemplary display of a 2D map of an unfolded patient skull for determining motor threshold location.

The aforementioned 2D map may be a 2D map of the unfolded patient skull as a way to guide the clinician during determination of the motor threshold. The 2D map may be created using various projection techniques. An example of the creation of a 2D map is shown in FIG. 4, and may include projecting the hand knob area of the brain onto the skin of the MRI image of a patient's skull. In FIG. 4, (a) is projected to the skin (b). An unfolding technique is used to flatten the patient's skull to a flat surface that is centered in (c). This unfolded 2D map is depicted in FIGS. 5 and 6. The origin of the spiral (depicted as "+") may be placed at the estimated center of the motor hand knob to minimize the amount of time that it takes to accurately determine the MT by maximizing the likelihood of receiving a hand twitch, including finger twitches. Instructions for the movement of the TMS coil to the desired target position may then be displayed on the screen so that the clinician may direct the coil to the initial target position (e.g., center of the spiral). Once the coil has reached the landmark, the clinician may be guided to search for the hand knob along the path (e.g., along the spiral) that is superimposed onto the 2D map of the brain.

Other projection techniques may be employed, e.g., from the simplest Mercator, to any stereographic projection algorithm where the geometry is inherently spherical and needs to be displayed on a flat surface.

In some variations, preference may be given to sections of the path (e.g., the spiral) that correspond to regions of high elevation in the brain (e.g., gyruses). In some cases, it is possible that a clinician could direct a pulse towards the motor hand knob without eliciting a hand or finger twitch. When this occurs, the pulse may have been directed towards a valley in the brain (e.g., sulcus), thus decreasing the likelihood of eliciting a hand or finger twitch due to charge roll-off. To overcome this problem, sections of preference on the aforementioned spiral may be identified by colors or shapes that signify regions of high elevation. Accordingly, clinicians may administer pulses at or near these regions in order to decrease the time necessary to determine MT.

Referring back to FIG. 5, an example of a MT location screen on a display of the neuronavigation system is shown. The screen includes a 2D map showing a cursor that represents the location of the coil. The center of the 2D map (e.g., spiral) may correspond to the location of the motor hand knob brain region. The pulse intensity color map is shown on the right side of the screen. A processor, e.g., a CPU, may carry out instructions to deliver a stimulus to the TMS coil. For each stimulus, the clinician may indicate whether a twitch or no twitch was observed by clicking buttons on the bottom of the screen. For each stimulus, a symbol may be displayed on the 2D map. The color of the symbol may correspond to the intensity as represented on the pulse intensity color map. If no twitch was found, the color will be gray. A live feed of coil location during stimulation is shown at the bottom left corner showing the area of the brain being treated as well as the orientation of the coil. FIG. 6 depicts an example of the MT Location screen after the MT location has been found. Clicking the "Ready to Proceed" button navigates to the screen to implement the ML-PEST algorithm to determine MT.

Coil orientation as well as position may be depicted on the bottom left of the MT Threshold Location screens (FIGS. 5 and 6). The angular position of the coil is shown on the map and a live feed of coil positioning is shown. This feature may help to improve coil placement and reduce the time needed to determine the motor threshold by improving accuracy of coil placement.

Figure 7:
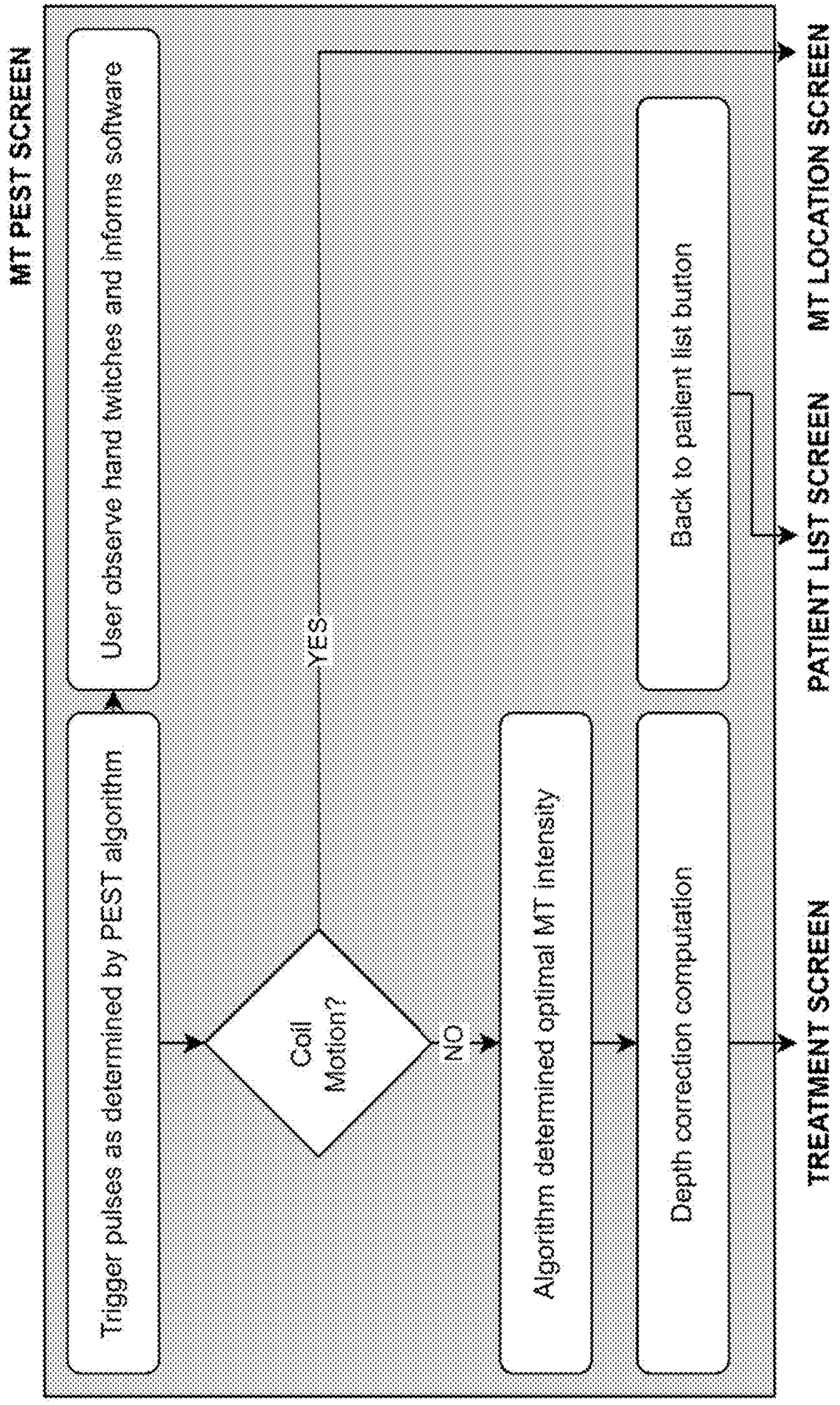
FIG. 7 is a flow chart depicting an exemplary method for determining a motor threshold.
Figure 8:
FIG. 8 depicts an exemplary display for determining a motor threshold level.

FIG. 7 depicts a flow chart that illustrates determination of the MT using the PEST algorithm. The first step may involve triggering TMS at a defined target (motor hand knob) to determine the motor threshold. If coil motion is observed, the clinician may navigate to the MT Location screen on the display. Once the stimulus is delivered, the clinician may confirm with the patient that the intensity is acceptable. If a twitch is observed on the screen/display, the clinician may indicate whether a hand twitch was observed due to stimulation of the motor hand knob. A button at the bottom of the MT PEST (FIG. 8) may be pressed to indicate twitch or no twitch. One or more computer processors may processes the twitch data entered and a mark may be annotated on the 2D chart displayed on the screen (FIG. 8). The bottom left side of the screen (FIG. 8) may show a smaller 2D map of the MT location shown on the MT Location screen (FIGS. 5 and 6). The result of the MT may be displayed on the screen. The MT may then be saved into memory of the one or more processors.

Figure 9:
FIG. 9 depicts an exemplary display for initiating treatment.
Figure 10:
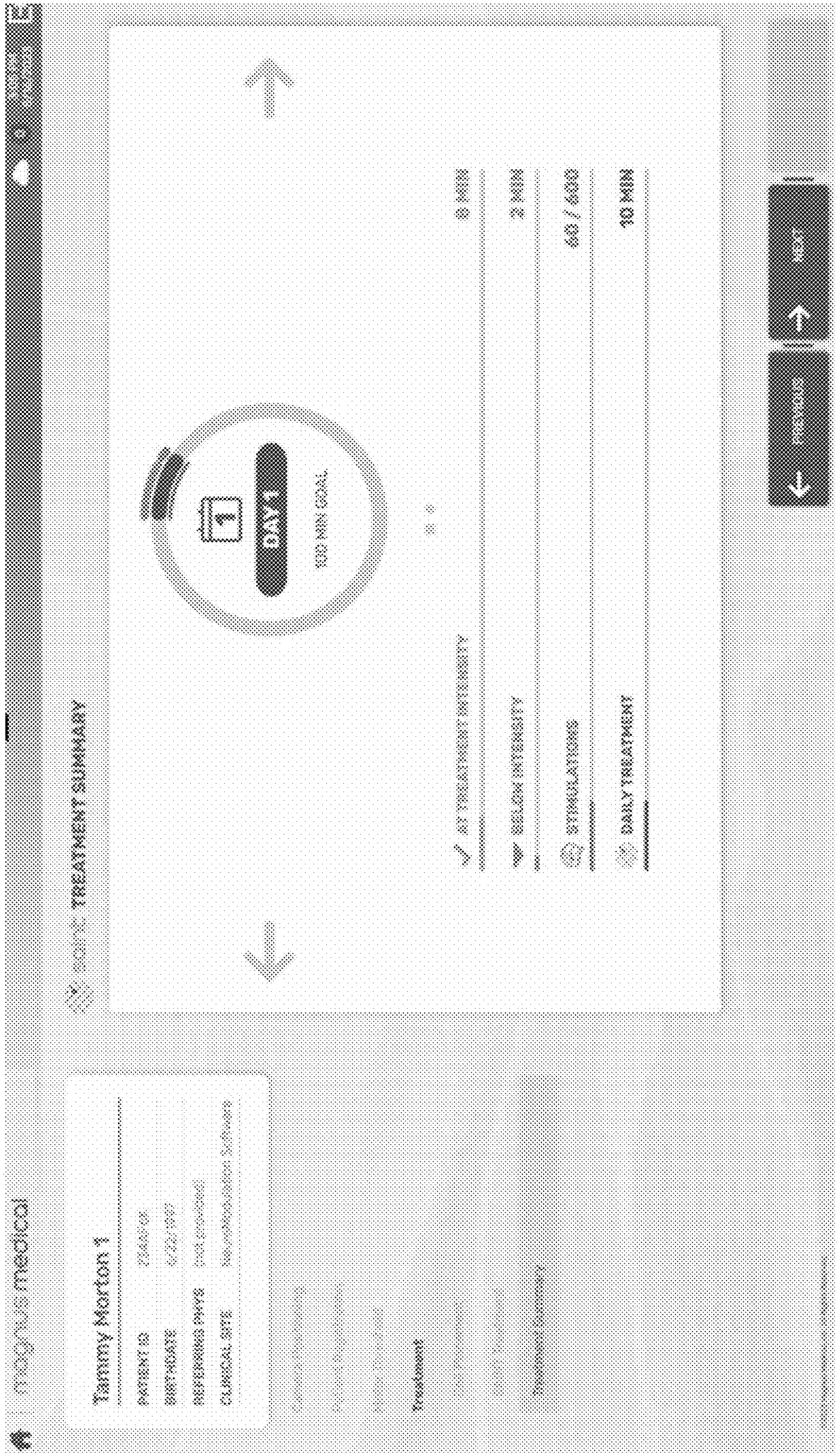
FIG. 10 depicts an exemplary display for post-treatment assessment of stimulation intensity.

Upon determining the MT, TMS therapy may be initiated. TMS therapy may be initiated at a level below the MT. The intensity of the TMS may be ramped up based on the patient's tolerance to stimulation. A switch at the bottom of the Treatment Session screen (FIG. 9) may be toggled to initiate automatic ramping of the TMS signal intensity. A chart that illustrates the ramping of intensity of the TMS signal is illustrated. The chart shows intensity with respect to percentage of MT. In some embodiments, the clinician may manually ramp up the TMS signal intensity. The intensity level may be determined based on patient tolerance to the stimulation. Once the optimal tolerance level is achieved, the treatment session is completed. Upon completion of the treatment session, a Treatment Summary screen (FIG. 10) may be shown. Each treatment session summary may include the amount of time at Treatment Intensity, time Below Intensity, the number of stimulations, and the total treatment time.

The neurostimulation delivered by the neurostimulation devices, e.g. a TMS coil, may be of various types. For example, the neurostimulation may be accelerated theta-burst stimulation (aTBS), such as accelerated intermittent theta-burst stimulation (aiTBS) or accelerated continuous theta-burst stimulation (acTBS). The neurostimulation may include applying iTBS pulse trains for multiple sessions per day over several days. In one variation, the neurostimulation may be delivered as a plurality of treatment sessions (e.g., one, two, three, four, five, six, seven, eight, nine, ten, or more than 10) on the same day for plurality of days (e.g., one, two, three, four, or five days). In some variations, the neurostimulation may be delivered for 10 sessions a day, with each session lasting 10 minutes, and an intersession interval (the interval between sessions) of 50 minutes.

The stimulation frequency of the TBS pulses may range from about 20 Hz to about 70 Hz, including all values and sub-ranges therein. For example, the stimulation frequency may be about 20 Hz, about 25 Hz, about 30 Hz, about 35 Hz, about 40 Hz, about 45 Hz, about 50 Hz, about 55 Hz, about 60 Hz, about 65 Hz, or about 70 Hz. When iTBS is used, the burst frequency (that is, the reciprocal of the period of bursting, for example if a burst occurs every 200 ms the burst frequency is 5 Hz) of the iTBS pulses may range from about 3 Hz to about 7 Hz, including all values and sub-ranges therein. For example, the burst frequency may be about 3 Hz, about 4 Hz, about 5 Hz, about 6 Hz, or about 7 Hz.

The patient may undergo multiple treatment sessions per day. In some variations, the number of treatment sessions per day may range from 2 sessions to 40 sessions. For example, the number of treatment sessions may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. The number of sessions for iTBS may range from 3 to 15 sessions per day. When cTBS is employed, the number of sessions may range from 10-40 sessions per day. The sessions may be performed on consecutive or non-consecutive days.

Additionally, the duration of the intersession interval may vary and range from about 25 minutes to about 120 minutes, including all values and sub-ranges therein. For example, the intersession interval may be about 25 minutes, about 30 minutes, about 35 minutes, about 40 minutes, about 45 minutes, about 50 minutes, about 55 minutes, about 60 minutes, about 65minutes, about 70 minutes, about 75 minutes, about 80 minutes, about 85 minutes, about 90 minutes, about 95 minutes, about 100 minutes, about 105 minutes, about 110 minutes, about 115 minutes, or about 120 minutes.

Transcranial magnetic stimulation is generally a neuropsychiatric therapy in which electric pulses are administered to the brain at a region, which when activated, may cause a desired downstream effect. However, this technology may be cumbersome to use due to the amount of energy that is needed to power high voltage instruments. Furthermore, treating an individual with electrical pulses may pose a safety risk as clinicians and patients are exposed to dangers such as dermal burns and electrocution. Even further, TMS generally may not have the capacity to stimulate deep brain structures.

In view of the foregoing, some variations of the systems and method described herein may employ focused ultrasound (fUS) to administer neurostimulation treatment. In contrast to using electricity, fUS generally employs sound to activate desired regions of the brain. In addition to being safer than TMS, fUS generally has the capacity to stimulate deep brain structures, which may allow clinicians to bypass stimulating cortical target regions. Additionally, fUS may be used at multiple target sites, or in conjunction with TMS, to provide multi-targeted neurostimulation therapy.

Systems for delivering neurostimulation to a patient are also described herein. In some variations, the systems may include a monitor having a screen configured to display an image of one or more of a head, brain, and skull of the patient, a neurostimulation device, and one or more processors configured to apply one or more machine learning algorithms to determine a location of the hand knob area of the patient. As previously described, the neurostimulation device may comprise a transcranial magnetic stimulation (TMS) coil. The one or more processors may be further configured to apply one or more machine learning algorithms to determine a motor threshold (MT) of the patient. In some variations, the one or more processors may be configured to control one or more neurostimulation parameters such as stimulation intensity. In other variations, the screen of the system display may provide instructions for movement of the neurostimulation device to a target location.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A method for determining a motor threshold of a patient comprising:

generating a two-dimensional (2D) map of a brain of a patient, wherein generating the 2D map comprises:

identifying a skin surface on a model of a head of the patient based on a magnetic resonance imaging scan of the head of the patient, determining a line normal to the skin surface such that a transcranial magnetic stimulation (TMS) coil when centered on the line is tangential to a skull of the head, projecting a first point representing a predetermined region of a motor cortex of the brain to a second point on the line normal to the skin surface, and creating a flattened representation of a skull of the patient with the projected point, wherein the flattened representation is centered around the second point;

defining a path comprising a spiral pattern centered around the second point on the 2D map;

delivering neurostimulation pulses at multiple positions along the defined path;

annotating each neurostimulation pulse positions on the 2D map with an amplitude of motor response;

determining a TMS coil location for stimulation based on the annotated neurostimulation pulse positions;

determining a motor threshold based on responses to a set of one or more neurostimulation pulses at the determined motor threshold location; and performing TMS therapy on the patient using the determined motor threshold, wherein the TMS therapy comprises delivering a series of magnetic pulses to the predetermined region of the motor cortex of the brain at an intensity based on the determined motor threshold.

2. The method of claim 1, wherein delivering neurostimulation pulses comprises adjusting an intensity of the neurostimulation pulses at different positions along the defined path.

3. The method of claim 1, wherein annotating each neurostimulation pulse position comprises indicating whether a motor response was observed for each neurostimulation pulse.

4. The method of claim 1, further comprising displaying the 2D map with the annotated neurostimulation pulse positions on a user interface in real time.

5. The method of claim 1, wherein determining the TMS coil location comprises identifying a cluster of annotated neurostimulation pulse positions that elicited motor responses.

6. The method of claim 1, further comprising adjusting a position of the TMS coil based on the determined TMS coil location.

7. The method of claim 1, wherein determining the motor threshold comprises using a parameter estimation by sequential testing (PEST) algorithm.

8. The method of claim 1, wherein the normal line is determined such that it minimizes the distance between the TMS coil and predetermined region of the motor cortex of the brain.

9. The method of claim 1, wherein the predetermined region of the motor cortex of the brain is a hand-knob area.

10. The method of claim 1, wherein the amplitude of the motor response is based on electromyogram (EMG) motor evoked potentials.

11. The method of claim 1, wherein the amplitude of the motor response is based on a visual twitch measurement.

12. A system for determining a motor threshold of a patient, comprising:

a set of one or more processors; and a set of one or more non-transitory computer-readable media comprising program instructions that are executable by the one or more processors such that the system is configured to:

generate a two-dimensional (2D) map of a brain of a patient, wherein generating the 2D map comprises:

identifying a skin surface on a model of a head of the patient based on a magnetic resonance imaging scan of the head of the patient, determining a line normal to the skin surface such that a transcranial magnetic stimulation (TMS) coil when centered on the line is tangential to a skull of the head, projecting a first point representing a predetermined region of a motor cortex of the brain to a second point on the line normal to the skin surface, and creating a flattened representation of a skull of the patient with the projected point, wherein the flattened representation is centered around the second point;

define a path comprising a spiral pattern centered around the second point on the 2D map;

deliver neurostimulation pulses at multiple positions along the defined path;

annotate each neurostimulation pulse positions on the 2D map as either twitch or no twitch;

determine a TMS coil location for stimulation based on the annotated neurostimulation pulse positions;

determine a motor threshold based on responses to a set of one or more neurostimulation pulses at the determined motor threshold location; and perform TMS therapy on the patient using the determined motor threshold, wherein the TMS therapy comprises delivering a series of magnetic pulses to the predetermined region of the motor cortex of the brain at an intensity based on the determined motor threshold.

13. The system of claim 12, wherein the defined path comprises a spiral pattern on the 2D map and delivering neurostimulation pulses comprises adjusting an intensity of the neurostimulation pulses at different positions along the defined path.

14. The system of claim 12, wherein:

annotating each neurostimulation pulse position comprises indicating whether a motor response was observed for each neurostimulation pulse; and the set of non-transitory computer-readable media further comprise program instructions that are executable by the set of processors such that the system is configured to display the 2D map with the annotated neurostimulation pulse positions on a user interface in real time.

15. The system of claim 12, wherein determining the motor threshold location comprises identifying a cluster of annotated neurostimulation pulse positions that elicited motor responses.

16. The system of claim 12, wherein determining the motor threshold comprises using a parameter estimation by sequential testing (PEST) algorithm.

17. The system of claim 12, wherein the predetermined region of the motor cortex is a hand-knob area.

* * * * *